United States Patent [19]

Wilk

[11] Patent Number: 5,305,748
[45] Date of Patent: Apr. 26, 1994

[54] MEDICAL DIAGNOSTIC SYSTEM AND RELATED METHOD

[76] Inventor: Peter J. Wilk, 185 West End Ave., New York, N.Y. 10023

[21] Appl. No.: 894,081

[22] Filed: Jun. 5, 1992

[51] Int. Cl.$^5$ .............................................. A61B 6/00
[52] U.S. Cl. ................................. 128/653.1; 607/154
[58] Field of Search .................. 128/653.1, 653.2, 804, 128/664, 665

[56] References Cited

U.S. PATENT DOCUMENTS 4,569,354  2/1986  Shapiro et al. ..................... 128/665

*Primary Examiner*—Ruth S. Smith
*Attorney, Agent, or Firm*—R. Neil Sudol; Henry D. Coleman

[57] ABSTRACT

In a medical diagnostic method a patient is supported in a predetermined position and microwave energy is focused on a predetermined target region in the patient to produce a burst of photoluminescence. Electromagnetic radiation emitted from organic cellular material at the focal point or the microwave radiation is automatically detected. In a subsequent step, a spectral output of the organic cellular material is automatically determined from electromagnetic radiation received from the radiation focal point through the patient during the step of detecting. In addition, a diagnosis of the excited cellular material is automatically implemented based on the results of the spectral analysis.

26 Claims, 1 Drawing Sheet

MEDICAL DIAGNOSTIC SYSTEM AND RELATED METHOD

BACKGROUND OF THE INVENTION

This invention relates to a system and an associated method for use in performing medical diagnoses. More particularly, this invention relates to a non-invasive diagnostic technique for determining molecular composition of tissue samples internal to a patient.

Substantial advances have been made in the last twenty years in ascertaining internal organic structures without surgery. CAT scanners and nuclear magnetic resonance (NMR) imaging devices, as well as ultrasonography, have provided the physician with powerful tools for use in diagnosing patients. However, although these tools provide images of internal organic structures such as tumorous growths, those tools cannot provide any information as to whether a growth is malignant or benign. Generally, to make a definitive diagnosis as to potential malignancy of cancerous growths in the internal tissues of a patient, an incision must be made and a sample of the suspect tissues removed in a biospy procedure. Such an invasive procedure is time consuming, expensive and traumatic to the patient.

OBJECTS OF THE INVENTION

An object of the present invention is to provide a new system and a related new technique for obtaining diagnostic information as to internal tissues of a patient.

Another object of the present invention is to provide such a system and method which provides diagnostic information as to internal tissues which is relatively non-invasive.

A further object of the present invention is to provide such a system and method which provides diagnostic information as to internal tissues without the performance of a biopsy.

A further object of the present invention is to provide such a system and device which is automated.

Other objects of the present invention will be apparent from the detailed descriptions and drawings included herein.

SUMMARY OF THE INVENTION

A medical diagnostic system comprises, in accordance with the present invention, a support for supporting a patient in a predetermined position, a radiation generator for generating electromagnetic energy having a predetermined range of wavelengths, and a focusing device disposed between the radiation generator and the patient support for focusing the energy at a predetermined point internal to the patient on the support. A photodetector assembly is disposed proximately to the patient support for detecting electromagnetic radiation emitted from organic cellular material at the predetermined point in the patient in response to excitation of the cellular material by the energy upon focusing thereof on the predetermined point by the focusing device. A computer is operatively connected to the photodetector assembly for determining a spectral output of the organic cellular material from signals generated by the photodetector assembly in response to radiation emerging from the patient.

Pursuant to another feature of the present invention, energy produced by the radiation generator is microwave energy. The radiation generator is preferably one of a plurality of microwave generators, while the focusing device includes a plurality of microwave lenses associated with respective ones of the generators.

According to another feature of the present invention, the radiation generator includes means for emitting the electromagnetic energy in pulses. In addition, the radiation generator may include means for varying the range of wavelengths.

Pursuant to an additional feature of the present invention, an aiming device is connected to the focusing device for enabling a change in the location of the focal point of the electromagnetic energy relative to the patient. The aiming device is preferably operatively connected to the computer for automatically varying the location of the focal point in accordance with a preprogrammed sequence.

Alternatively, to change the focal point's location, a mechanism is connected to the patient support for shifting the position of the patient, thereby changing the location of the predetermined point relative to the patient.

Pursuant to another feature of the present invention, the computer includes memory and programming for compensating for differential absorption of the spectral output by organic tissues of the patient between the radiation focal point and the photodetector assembly. Also, the computer includes memory and programming for automatically diagnosing the condition of the organic cellular material from the spectral output.

According to a further feature of the present invention, the photodetector assembly includes an array of individual photodetectors disposed in an arc about the patient support.

A medical diagnostic method comprises, in accordance with the present invention, the steps of (a) supporting a patient in a predetermined position, (b) generating electromagnetic energy having a predetermined range of wavelengths, (c) focusing the energy at a predetermined point internal to the patient, (d) transmitting the energy through the patient to the predetermined point, and (e) automatically detecting electromagnetic radiation emitted from organic cellular material at the predetermined point in response to excitation of the cellular material by the focused electromagnetic energy. In a subsequent step (f), a spectral output of the organic cellular material is automatically determined from electromagnetic radiation received from the radiation focal point through the patient during the step of detecting.

The method may further comprise the step of automatically varying, in accordance with a preprogrammed sequence, the range of wavelengths produced during the generating step.

Pursuant to another feature of the present invention, the location of the radiation focal point is automatically varied, for example, by automatically moving the patient support or by acting on a focusing device. The location of the radiation focal point may be automatically changed in accordance with a preprogrammed sequence. The changing of the focal point causes a continual or repeatable luminescent emission of radiation from cellular or organic material within a predefined region, thereby increasing the amount of radiation collected during the step of detecting and thereby facilitating a determination of the spectral emission by the target region.

The target region is predetermined by using a conventional non-invasive internal structure monitoring machine, e.g., a CAT scanner or an NMR imaging apparatus. The location of the target region may be manually input to the computer of a system in accordance with the present invention. Alternatively, the computer may be connected to a CAT scanner or NMR imaging apparatus, whereby the location of the target region may be fed from the structural monitoring machine to the computer.

According to another feature of the present invention, the method further comprises the step of automatically compensating for differential absorption of the spectral output by organic tissues of the patient between the predetermined point and an outer skin surface of the patient. Another step of a method in accordance with the present invention is automatically diagnosing the condition of the organic cellular material from the spectral output.

Pursuant to another feature of the present invention, the step of detecting is implemented throughout an arc about the supported patient.

Pursuant to an additional feature of the present invention, the electromagnetic excitation energy is emitted at a plurality of different output locations disposed about the patient. Moreover, the electromagnetic excitation energy is preferably emitted in pulses.

A system and a technique in accordance with the present invention obtains diagnostic information as to internal tissues of a patient in a relatively non-invasive way. No incisions are necessary. No conventional biopsy is performed.

DETAILED DESCRIPTION

Figure 1:
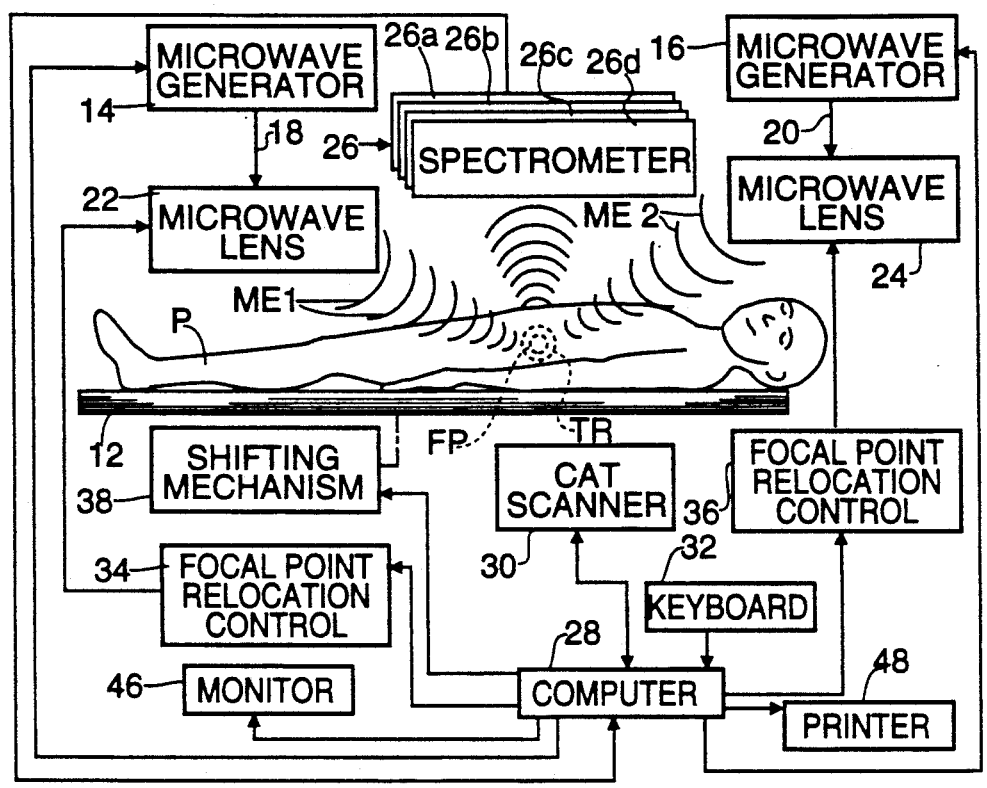
FIG. 1 is a block diagram of a medical diagnosis system in accordance with the present invention.

As illustrated in FIG. 1, a medical diagnosis system comprises a support 12 for supporting a patient P in a predetermined position and a plurality of microwave radiation generators 14 and 16 for generating electromagnetic energy having a predetermined range of wavelengths in the microwave region of the electromagnetic spectrum. Each microwave radiation generator 14 and 16 is connected via a wave guide 18 or 20 to a respective focusing device or microwave lens 22 or 24. Lenses 22 and 24 are disposed between the respective radiation generator 14 and 16 and patient support 12 for focusing microwaves ME1 and ME2 at a predetermined focal point FP internal to a target region TR inside patient P.

A photodetector assembly or spectrometer assembly 26 comprising a plurality of individual photodetectors or scanning spectrometer 26a, 26b, 26c, 26d is disposed proximately to patient support 12 for detecting electromagnetic radiation ER from the patient P. Radiation ER is emitted from organic cellular material at predetermined focal point FP in response to excitation of the cellular material by the microwaves ME1 and ME2. Generally, molecules in a limited number of cells in target region TR are excited by the incoming microwaves ME1 and ME2 to photoluminesce and emit radiation ER. A part of radiation ER escapes through overlying organic tissues of the patient P and is detectable by photodetector assembly or spectrometer assembly 26.

The cells containing the excited molecules are generally destroyed upon excitation by microwaves EM1 and EM2. However, the focus is controlled by lenses 22 and 24 to limit the area which is affected in any one excitation step. The size of focal point FP is also limited in part by pulsing the microwave energy.

A computer 28 is operatively connected to photodetector assembly 26 for analyzing the signals from the photodetector assembly to ascertain a spectral output of the organic cellular material which luminesced at focal point FP. Inasmuch as the spectral content of the escaping radiation ER is differentially modified by the tissues through which the radiation passes, computer 28 must be programmed to approximate the original spectral content of the radiation emitted by the excited molecular or cellular material at focal point FP. To that end, computer 28 is previously programmed to store known absorption spectra for different kinds of tissue. In addition, computer 28 is provided with three-dimensional structural data as to the organs of patient P surrounding target region TR. That structural data is provided by a CAT scanner or NMR imaging apparatus 30 connected to computer 28. From the kinds and thicknesses of the tissues between focal point FP and a respective unit 26a, 26b, 26c, or 26d of photodetector assembly 26, computer 28 is able to reconstruct the original spectral content of the radiation ER emitted in a photoluminescence process by the excited organic material at focal point FP.

Computer 28 is connected to generators 14 and 16 for controlling such parameters as the rate of pulsing, the interpulse interval, the pulse duration and the intensity of the radiation. These parameters may be preset by an operator via a keyboard 32. In addition, the spectral range of the microwave energy produced generators 14 and 16 may be adjusted in response to signals from computer 28. Furthermore, computer 28 may be instructed via keyboard 32 to automatically vary the microwave output of generators 14 and 16 during a single diagnostic procedure on patient P.

It is to be noted that a plurality of microwave generators 14 and 16, with their respective focusing lenses 22 and 24, are provided in part to minimize the amount of radiation absorbed by tissues outside of target region TR. It is only at focal point FP that the microwave energy is sufficiently intense to cause photoluminescence with its concomitant destruction of biological cells.

Target region TR is predetermined through computer-aided tomography as implemented by CAT scanner 30 or through the use of an NMR imaging apparatus. The location of target region TR may be manually input to computer 28. Alternatively, computer 28 is connected to CAT scanner or NMR imaging apparatus 30, whereby the location of target region TR may be automatically fed therefrom to computer 28.

As further illustrated in FIG. 1, computer 28 is connected to a pair of focal point relocation control units 34 and 36 in turn connected to respective microwave lenses 22 and 24. In response to signals from computer 28, control units 34 and 36 can continually or periodically change the location of focal point FP in accordance with a preprogrammed sequence, thereby to enabling a continual or repeatable luminescent emission of radiation from cellular or organic material within target region TR. This procedure increases the amount of radiation collected by photodetector assembly 26, thereby facilitating a determination of the spectral emission by target region TR. Within limits imposed, for example, by the size of target region TR, the microwave excitation and photoluminescence process can be continued until computer 28 has acquired sufficient data to diagnose the tissues of target region TR, for example, as malignant or benign.

As an alternative or supplement to relocation control units 34 and 36, a shifting mechanism 38 is connected to patient support 12 and computer 28 for shifting the position of the patient P under the control of computer 28, thereby changing the location of the focal point FP relative to the patient.

Figure 2:
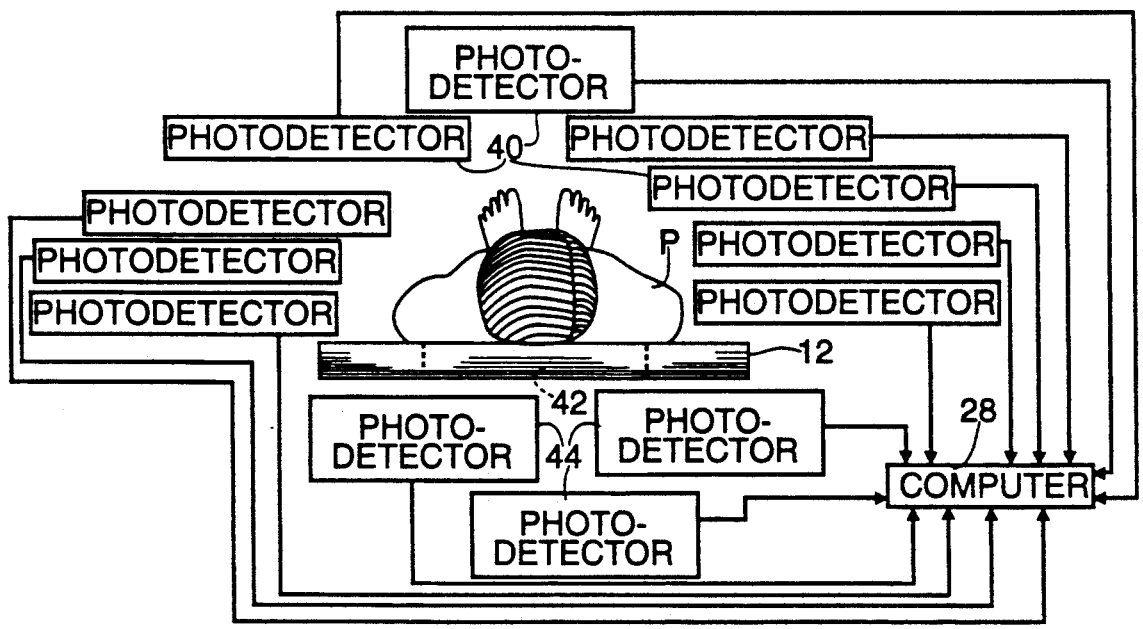
FIG. 2 is a block diagram showing details of a preferred embodiment of the medical diagnosis system of FIG. 1.

As depicted in FIG. 2, photodetector assembly 26 may include an array of individual photodetectors 40 disposed in an arc or annular array about patient support 12. To increase the amount of collectible data, support 12 may be formed with an opening 42 so that photodetectors 44 may be disposed below patient P.

Computer 28 is connected to peripheral output devices such as a monitor 46 and a printer 48 (FIG. 1) for communicating the results of spectral analyses and automatic diagnoses to a user.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical tissue investigation system comprising:
   support means for supporting a patient in a predetermined position;
   generating means for generating electromagnetic energy having a predetermined plurality of wavelengths;
   focusing means disposed between said generating means and said support means for focusing said energy at a predetermined point internal to the patient supported on said support means;
   photodetector means disposed proximately to said support means for detecting electromagnetic radiation emitted from organic cellular material at said predetermined point in response to excitation of said cellular material by said energy upon focusing thereof on said predetermined point by said focusing means; and
   computer means operatively connected to said photodetector means for determining a spectral output of said organic cellular material.

2. The system defined in claim 1 wherein said energy is microwave energy.

3. The system defined in claim 2 wherein said generating means includes a plurality of microwave generators, said focusing means including a plurality of microwave lenses associated with respective ones of said generators.

4. The system defined in claim 2 wherein said generating means includes means for transmitting said microwave energy in pulses.

5. The system defined in claim 1 wherein said generating means includes means for varying said wavelengths.

6. The system defined in claim 5 wherein said generating means is operatively connected to said computer means for automatically varying said wavelengths in accordance with a preprogrammed sequence.

7. The system defined in claim 1, further comprising aiming means connected to said focusing means for enabling a change in the location of said predetermined point.

8. The system defined in claim 7 wherein said aiming means is operatively connected to said computer means for automatically varying the location of said predetermined point in accordance with a preprogrammed sequence.

9. The system defined in claim 1, further comprising shifting means connected to said support means for shifting the position of the patient, thereby changing the location of said predetermined point relative to the patient.

10. The system defined in claim 1 wherein said computer means includes means for compensating for differential absorption of said spectral output by organic tissues of said patient between said predetermined point and said photodetector means.

11. The system defined in claim 1 wherein said computer means includes means for automatically diagnosing the condition of said organic cellular material from said spectral output.

12. The system defined in claim 1 wherein said photodetector means includes an array of individual photodetectors disposed in an arc about said support means.

13. The system defined in claim 1 wherein said generating means includes means for transmitting said energy in pulses.

14. A medical tissue investigation method comprising the steps of:
   supporting a patient in a predetermined position;
   generating electromagnetic energy having a predetermined plurality of wavelengths;
   focusing said energy at a predetermined point internal to the patient;
   transmitting said energy through the patient to said predetermined point;
   automatically detecting electromagnetic radiation emitted from organic cellular material at said predetermined point in response to excitation of said cellular material by said energy upon focusing thereof on said predetermined point; and
   automatically determining a spectral output of said organic cellular material from electromagnetic radiation received from said predetermined point through the patient during said step of detecting.

15. The method defined in claim 14, further comprising the step of varying said wavelengths.

16. The method defined in claim 15 wherein said step of varying said wavelengths is automatically implemented in accordance with a preprogrammed sequence.

17. The method defined in claim 14, further comprising the step of changing the location of said predetermined point.

18. The method defined in claim 17 wherein said step of changing the location of said predetermined point is automatically implemented in accordance with a preprogrammed sequence.

19. The method defined in claim 17 wherein said step of changing includes the step of automatically moving said patient from said predetermined position to another position.

20. The method defined in claim 17 wherein said step of changing is automatically implemented in said step of focusing by focusing said energy at another point internal to the patient and different from said predetermined point.

21. The method defined in claim 14, further comprising the step of automatically compensating for differential absorption of said spectral output by organic tissues of said patient between said predetermined point and an outer skin surface of the patient.

22. The method defined in claim 14, further comprising the step of automatically diagnosing the condition of said organic cellular material from said spectral output.

23. The method defined in claim 14 wherein said step of detecting includes the step of operating a detector at a first location to monitor electromagnetic radiation emitted from organic cellular material at said predetermined point, said step of detecting further including the step of operating a detector at a second location spaced from said first location to monitor electromagnetic radiation emitted from organic cellular material at said predetermined point.

24. The method defined in claim 14 wherein said energy is microwave energy.

25. The method defined in claim 14 wherein the step of generating includes the step of emitting said energy at a plurality of spaced output locations disposed about the patient.

26. The method defined in claim 14 wherein said step of generating includes the step of transmitting said energy in pulses.

* * * * *